(12) United States Patent
Friboulet et al.

(10) Patent No.: US 7,109,291 B2
(45) Date of Patent: Sep. 19, 2006

(54) COMPOUNDS CAPABLE OF MODULATING THE ACTIVITY AND STIMULATING THE PRODUCTION OF A CATALYTIC ANTIBODY

(75) Inventors: Alain Friboulet, Jonquieres (FR); Berangere Avalle-Bihan, Compiegne (FR); Helene Debat, Sainte Dode (FR); Daniel Thomas, Villers sur Coudun (FR)

(73) Assignee: Gradient, Compiegne (FR)

( * ) Notice: Subject to any disclaimer, the term of this patent is extended or adjusted under 35 U.S.C. 154(b) by 0 days.

(21) Appl. No.: 10/716,030

(22) Filed: Nov. 17, 2003

(65) Prior Publication Data

US 2004/0138124 A1    Jul. 15, 2004

Related U.S. Application Data

(63) Continuation of application No. PCT/FR02/01730, filed on May 22, 2002.

(30) Foreign Application Priority Data

May 22, 2001   (FR) .................................. 01 06754

(51) Int. Cl.
*A61K 38/04* (2006.01)
(52) U.S. Cl. ..................................... 530/330
(58) Field of Classification Search ................ 530/383
See application file for complete search history.

(56) References Cited

U.S. PATENT DOCUMENTS 5,948,658 A    9/1999    Landry 6,048,717 A    4/2000    Paul
6,235,714 B1   5/2001    Paul

FOREIGN PATENT DOCUMENTS

| DE | 3841767 | * | 12/1988 |
| WO | WO 90/06939 | * | 6/1990 |
| WO | WO 96/34887 | * | 11/1996 |
| WO | WO 99/48925 |   | 9/1999 |

OTHER PUBLICATIONS

Biotechterms.org, analogue, 2001, http://biotechterms.org/sourcebook/saveidretrieve.php3?id=99, printed Sep. 20, 2004, p. 1.*
Lefevre et al., "A suicide-substrate mechanism for hydrolysis of beta-lactams by an anti-idiotypic catalytic antibody." FEBS Lett. 489(1):25-8 (2001).
Du et al., "A New Monoclonal Anti-idiotypic Catalytic Antibody with a CPA-like Activity." Bioorg. & Med. Chem. Lett. 9:1487-1492 (1999).

* cited by examiner

*Primary Examiner*—Bruce R. Campbell
*Assistant Examiner*—Jennifer Ione Harle
(74) *Attorney, Agent, or Firm*—Fish & Richardson P.C.

(57) ABSTRACT

The invention concerns novel compounds capable of modulating the activity and stimulating the production of catalytic antibodies. More particularly, the invention concerns a compound capable of increasing the activity of an antibody having specific affinity for the catalytic site of the antibody, and it is not immunogenic. Such compounds are useful in particular for therapeutic treatment or prevention of a pathology related to an enzymatic deficiency, to stimulate in vivo hydrolysis of xenobiotics, drugs, medicines or any other molecule potentially toxic for the organism or for preventing or inhibiting allergic reactions.

5 Claims, 1 Drawing Sheet

Figure 1:
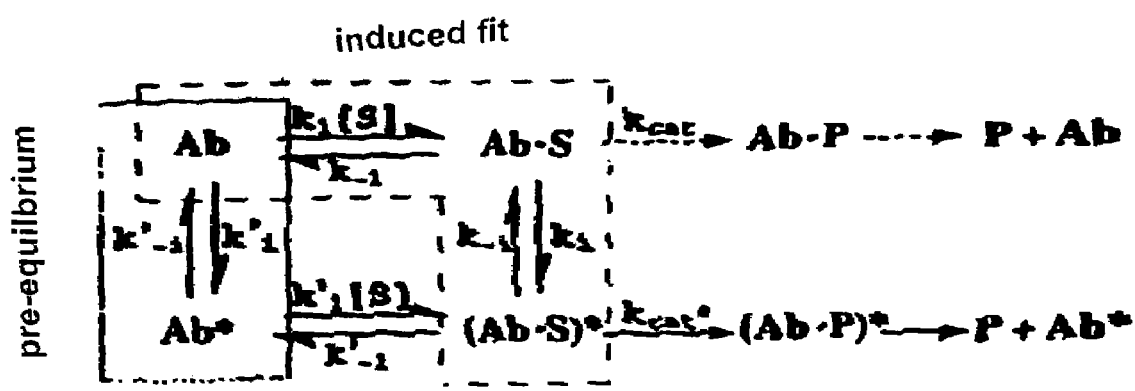

//  COMPOUNDS CAPABLE OF MODULATING THE ACTIVITY AND STIMULATING THE PRODUCTION OF A CATALYTIC ANTIBODY

This application is a continuation (and claims the benefit of priority under 35 USC 120) of U.S. application Ser. No. PCT/FR02/01730, filed May 22, 2002. The disclosure of the prior application is considered part of (and is incorporated by reference in) the disclosure of this application.

The invention relates to novel compounds capable of modulating the activity and stimulating the production of catalytic antibodies. In particular, the invention concerns a compound capable of increasing the activity of a catalytic antibody, characterized in that it has a specific affinity for the catalytic site of said antibodies, and in that it is non immunogenic. Such compounds are of particular use in the therapeutic treatment or prevention of a disease linked to an enzymatic deficiency, to stimulate, in vivo, the hydrolysis of xenobiotics, drugs, medication or any other molecule that is potentially toxic to the organism or to prevent or impede allergic reactions.

Antibodies and enzymes both have the property of specifically recognizing molecules. With the exception of pathological cases, the antibody recognizes an antigen or a molecule that is foreign to the organism producing the antibody. Binding of the antibody to the antigen generally results in neutralization of the foreign molecule. Enzymes are biological catalysts which bind to a molecule in such a way that the activation energy of a reaction involving that molecule is reduced, thereby increasing the reaction rate.

In 1946, Linus Pauling proposed the following concept: antibodies would preferentially bind the stable states of molecules, while enzymes would preferentially bind the transition state with a higher energy state rather than the molecule of substrate in its low energy state. According to Pauling's hypothesis (L Pauling, Nature (1948) 161: 707), the enzyme would stabilize the transition state of the molecules, reducing the activation energy of a reaction and thereby increasing the rate of that reaction.

By following that hypothesis, he proposed a strategy for obtaining novel catalytic activities based on the production of antibodies directed against a hapten that mimics the transition state of a given reaction, termed the TSA (transition state analogue). Thus, an antibody directed against such antigens should acquire similar catalytic properties to those of enzymes.

That strategy has been confirmed many times since 1986. Catalytic antibodies can be induced by immunizing an animal with a transition state analogue (TSA) rendered immunogenic (Pollack et al, J Am Chem Soc (1988) 110: 8713, Jackson et al, PNAS (1988) 85: 4953, Shokat et al, Chem Int Ed Engl (1988) 27: 1172) and are capable of catalyzing different types of chemical reaction. Since the first results demonstrating the possibility of inducing the production of antibodies catalyzing the hydrolysis reaction of esters and carbonates, more than 70 different reactions have been catalyzed by antibodies. Those reactions concern both the hydrolysis of chemical bonds (esters, amides, Diels-Alder additions, . . . ) and isomerization, decarboxylation, oxido-reduction reactions, etc. . . .

In parallel, antibodies with a catalytic activity have been isolated from the serum of patients with different diseases. The first demonstrations were made by purifying the antibodies from human serum. Those "natural" catalytic antibodies have DNAse or protease activity. In particular, catalytic antibodies having a protease activity against the vasoactive intestinal peptide (VIP) were isolated from the serum of patients with asthma. Those same antibodies could be obtained by immunizing mice with the same immunogenic peptide (Paul et al, J Neuroimmunol (1989) 23: 133–142). Others with protease activities were extracted, which cleaved thyroglobulin in patients with Hashimoto's Thyroiditis or factor VIII in hemophiliacs treated with that coagulation factor (INSERM, Bayer Pharma, 1999, European patent EP-A-0 1 074 842). A catalytic DNA hydrolysis activity was demonstrated in the serum of patients with lupus erythematosus or rheumatoid arthritis (Shuster A M et al, Science (1992) 256: 665–667). It appears that this DNAse activity is correlated with symptoms of these diseases.

A further route for the production of catalytic antibodies has recently been proposed, based on the preparation of anti-idiotypic antibodies mimicking the catalytic site of an enzyme. As an example, it has been shown that is possible to induce, in vivo, the production of anti-idiotypic catalytic antibodies with a β-lactamase activity by immunization with an antibody directed against the active site of β-lactamase (Avalle B et al, Faseb J, (1998) 12: 1055–1060).

Catalytic antibodies have many applications. In particular, catalytic antibodies would be useful in catalyzing chemical reactions that are not carried out by natural enzymes, in particular to act in vivo on the metabolism (medical application) or to carry out particular chemical reactions (industrial application).

Because of the vast range of specificity of antibodies and also of their involvement in the processes of acquired immunity, allergies and auto-immunity, the interest in providing in vivo production of catalytic antibodies, in particular for their therapeutic applications, can readily be understood.

One application which has been developed concerns the use of the hydrolytic properties of catalytic antibodies to activate non toxic compounds into cytotoxic compounds (Zeneca Ltd, 1998, U.S. Pat. No. 5,807,688). By targeting that activity to target cells, molecules the cytotoxicity of which has been masked with a chemical group could be activated in contact with tumor cells for anti-cancer treatments (ADAPT method, antibody-directed abzyme prodrug therapy). A further example concerns the capacity of certain antibodies to hydrolyze cocaine. The development of an antibody with such properties could allow its use in treating overdoses and cocaine addiction. The patent describes a method for inducing the stimulation of catalytic antibody by dint of immunizing a mammal with a hapten, an analogue of transition states (Barber et al, 2000, U.S. Pat. No. 6,017, 541). A third example has been developed by Advanced Biotech, which produces catalytic antibodies for the treatment of infections by gram-negative bacteria to obtain the endotoxin (Genetic Engineering News (1999), vol 19, no° 20, page 15).

Theoretically, research aimed at producing antibodies capable of hydrolyzing a specific molecule and in particular a polypeptide could result in the design of novel therapeutic treatments, in particular treatments of a particular enzymatic deficit, anti-viral treatments, treatments of xenobiotics potentially toxic to the organism, or allergy prevention methods.

However, to be effective in such applications, the catalytic activities of those antibodies must be sufficiently significant as regards the desired effect.

Methods based on the design of haptens that can induce the in vivo production of catalytic antibodies (Igen International Inc, 1989, EP-A-0 413 762), immunization strategies (Boston Biomedical Research Institute, 2000, U.S. Pat. No.

6,140,091), the site-directed modification of antibodies or screening methods (catELISA, Tawfik et al, PNAS (1993) 90: 373–377) and selection (phage display) (Smith et al, 1999, U.S. Pat. No. 5,855,885) have significantly improved the catalytic properties of certain antibodies and/or their production in vivo.

However, those methods are applicable on a case by case basis and are frequently insufficient as regards obtaining efficacy compatible with medical or industrial use. Thus, there is still a need to identify novel methods that can improve the catalytic properties of catalytic antibodies or induce novel catalytic activities.

It has recently been shown that substrates for catalytic antibodies can in vitro form a stereospecific interaction different from the antigen-antibody complex and induce a modification to the antibody conformation, that modification increasing the affinity of the catalytic antibody for its substrate (Lindner et al, J Mol Biol (1999) 285: 421–430). In particular, an analysis of anti-idiotypic antibodies has shown that the catalytic site cohabits in the space containing the zone for recognizing an immunogen without being confused therewith. It has also been shown that it is possible to keep the immune function and lose the catalytic function of an antibody (Kolesnikov et al, PNAS (2000) 97: 13526–13531), suggesting that the functional zone of the catalytic antibody carries out two clearly different functions (specific immune response or catalysis) and that in that zone, competition exists to complex potentially different molecules (antigen or substrate).

The invention results from the discovery that it is possible to modulate in vivo the activity of a catalytic antibody using a non immunogenic compound with a specific affinity for a catalytic site of said antibody. Such compounds have a direct effect on catalytic activity by inducing a conformational change on antibodies already produced. Further, and particularly surprisingly, the inventors have shown that, despite the non immunogenic nature of these compounds, they can indirectly increase the production of catalytic antibodies by displacing the equilibrium of the immune system towards the production of antibody with an increased catalytic activity, that displacement being induced by the conformational change in pre-existing antibodies.

Thus, the invention concerns a compound capable of modulating the activity of a catalytic antibody, said compound being characterized in that it has a specific affinity for the catalytic site of said antibody, and in that it is non immunogenic.

It also concerns a method for modulating the activity of a catalytic antibody, comprising brining said antibody into contact with a non immunogenic compound having a specific affinity for the catalytic site of said antibody.

A catalytic antibody is an antibody that is capable of specifically but not exclusively recognizing two types of molecule:

the antigen or immunogen, i.e. a molecule that can induce a direct immune response by activating specific B or T lymphocytes depending on the nature of the antigen; and the substrate, which specifically recognizes the catalytic site of the antibody and, as its name indicates, is the substrate for the chemical reaction catalyzed by the catalytic antibody.

The term "non immunogenic compound" means a compound that is incapable of directly activating specific B or T lymphocytes (clonal selection). Clearly, it should be kept in mind that such non immunogenic compounds are capable of increasing in vivo the production of catalytic antibodies in an indirect manner when they have a specific affinity for the catalytic site of the antibody, by the mechanism described below:

The catalytic antibodies can be in two isoforms: a "non active" or "slightly active" isoform (hereinafter termed Ab) and an "active" isoform (hereinafter termed Ab*). The active isoform (Ab*) has a catalytic activity (hereinafter termed $k_{cat}$*) that is higher than that of the non active isoform (hereinafter termed $k_{cat}$). In the presence of a compound (S) in accordance with the invention, binding of said compound to the catalytic antibody to form the complex (Ab,S) displaces the equilibrium towards the formation of the complex (Ab*, S), a phenomenon which is related to the allosteric behavior shown in FIG. 1. The change in conformation induced by the compound of the invention then leads to in vivo modulation of the catalytic activity of the antibody which changes from the value $k_{cat}$ to a value $k_{cat}$*, $k_{cat}$* being different from $k_{cat}$.

The catalytic activity can thus be modulated for catalytic antibodies present in the serum of patients by injecting the compounds of the invention in the form of pulses, using methods analogous to those employed for a vaccine.

Preferably, a compound of the invention is capable of increasing the activity of a catalytic antibody.

The conformational change of the isoform Ab to isoform Ab* can also result in vivo in indirect stimulation of the production of novel antibodies. Thus, in the preferred implementation of the invention, a compound of the invention as defined above is capable of stimulating the production of the catalytic antibody the activity of which has been enhanced by it.

The term "stimulating production" means it is not de novo production of antibodies but an increase in the production of pre-existing antibody, for example as a result of a first immunization with an antigen.

Depending on the desired applications of a compound of the invention, the compound is advantageously selected from the group comprising:

a substrate of an enzyme or an analogue thereof, inhibitor or activator;

a ligand binding itself to a receptor, in particular a hormone, a drug, a medication or a fragment or analogue thereof;

an antibiotic or an analogue thereof;

a viral, bacterial or parasitic polypeptide;

a recalcitrant and potentially toxic xenobiotic; or an allergen analogue.

The term "analogue of an enzyme substrate" means non immunogenic substrates of an enzyme and derivative molecules, in particular stable analogues of the non immunogenic transition states of an enzyme or non immunogenic inhibitors or activators of said enzyme. Examples of analogues of the enzyme substrate of the invention are antibody fragments specifically recognizing the catalytic site of an enzyme.

Said compounds are capable of increasing in vivo the catalytic activity and/or production of catalytic antibodies for which they exhibit an affinity and can thus compensate for the deficient or reduced enzymatic activity resulting from a disease or a therapeutic treatment, for example.

Examples of deficient or reduced enzymatic activities following a disease or a therapeutic treatment are hydrolase type activities, in particular peptidase, protease, oxidoreductase activities (for example dehydrogenase, oxidase or oxygenase), isomerase activities, lyase activities, in particular decarboxylase, transferase activities and in particular kinase activities, and ligase activities.

The following constitute examples of diseases that can be cited:
- chronic hemolytic anemia, which is the consequence of a deficit of triose phosphate isomerase;
- leucinosis, which is the consequence of a keto-acid decarboxylase deficiency;
- Lesch-Nyhan syndrome, which is the consequence of deficient hypoxanthine guanine phosphoribosyl transferase;
- Type II glutaric aciduria, which is the consequence of deficient acyl CoA dehydrogenase; or
- hyperglycerolemia, which is the consequence of a glycerol kinase deficiency.

It is important to emphasize here that, surprisingly, a compound in accordance with the invention, which is an enzyme inhibitor, is capable of increasing the catalytic activity of a catalytic antibody mimicking the activity of that enzyme, via its specific properties as regards catalytic antibodies, described above, despite its inhibiting properties.

An enzyme substrate or analogue falling within the definition of the compounds of the invention can thus, for example, depending on the nature of the enzyme for which is it a substrate, be a peptide, but also a sugar or one of its derivatives, a lipid or one of its derivatives, a nucleotide or one of its derivatives, or a steroid or one of its derivatives.

One example of such an analogue of an enzyme substrate is a non immunogenic inhibitor of β-lacatamase activity, oral injection of which can induce the production of antibodies hydrolyzing antibiotics with a β-lactame ring. One particular compound of the invention is a peptide with an affinity for the active site of β-lactamase, and more preferably is characterized in that it specifically inhibits β-lactamase activity.

The invention also pertains to a compound that can increase, in vivo, the physiological level of an enzymatic activity, characterized in that it comprises a non immunogenic substrate of a catalytic antibody having said enzymatic activity or one of its activator or inhibitor analogues and in that it has a specific affinity for the catalytic site of said antibody.

In a further preferred implementation of the invention, a compound of the invention is a ligand that binds to a receptor and in particular a hormone, a drug, a medication, or one of its fragments or analogues.

Depending on the implementation, the compounds described above are capable of increasing the catalytic activity of catalytic antibodies degrading drugs, hormones or medication from which they derive or of which they are analogues.

Thus, the invention also pertains to a compound that can stimulate, in vivo, the degradation of drugs or medication by specific catalytic antibodies, characterized in that it is non immunogenic, it comprises a drug or a medication or a fragment or analogue thereof and in that it has a specific affinity for the catalytic site of said antibody.

The fragments of a ligand forming part of the definition of a compound of the invention are selected from fragments that have retained the ability to bind to the receptor. When the ligand is a polypeptide, the ligand fragments are peptides that retain the ability to bind to the receptor.

An analogue of a ligand is a molecule that is capable of binding to the same receptor as the ligand. In particular, it is an agonist or an antagonist of the receptor onto which the ligand binds. Such an analogue can be a natural or artificial molecule isolated by screening molecules binding to a receptor. One example of such a ligand is a fragment of TNF-α falling within the definition of the compounds of the invention and capable of binding to cell receptors p55 and p75.

In particular, a preferred compound is characterized in that it comprises a peptide derived from the cytokine TNFα, said compound being non immunogenic and having a specific affinity for the catalytic site of a catalytic antibody and said peptide contains one of the following amino acids sequences:

LNRRA (SEQ ID NO:1), IASVY (SEQ ID NO:2) or LFA.

A further example of the preferred compound is characterized in that it comprises a peptide derived from thyroglobulin.

A further preferred example of a compound is codeine, a cocaine analogue capable of stimulating the production of catalytic antibodies degrading cocaine by repeated injection.

In a further preferred implementation of the invention, a compound of the invention is selected from antibiotics or their analogues. The term "antibiotic analogue" means a molecule with a structure that differs from the antibiotic molecule of which it is an analogue but capable of reproducing a similar "antibiotic" function.

In a further preferred implementation of the invention, a compound of the invention is selected from a viral, bacterial or parasitic peptide.

Such compounds are capable of stimulating catalytic production degrading viral bacterial or parasitic proteins and thus combating viral, bacterial or parasitic infections.

Particularly preferred examples of peptides are non immunogenic peptides derived from surface epitopes or virulence proteins of pathogenic organisms such as HIV, HSV or HBV, pathogenic bacteria such as *Legionella, Listeria, Staphylococcus*, or parasites such as *P. falciparum, Echinococcus, Leishmania* or *Trypanosoma*.

One particular example of such a compound of the invention is a compound characterized in that it comprises a non immunogenic peptide derived from a Herpes virus epitope.

In a further preferred implementation of the invention, a compound of the invention is a recalcitrant xenobiotic that is potentially toxic or a fragment thereof. The term "recalcitrant xenobiotic" means any molecule foreign to an organism that can accumulate in the tissues or the internal medium of man or animal. Certain of such molecules, and in particular pesticides (organophosphorous compounds), dioxin or organochlorinated compounds (PCB, DDT, . . . ) are potentially toxic to the organism, in particular in the long term.

The accumulation of certain xenobiotics in the organism is cancerigenic or neurotoxic.

As a result, the invention pertains to a compound that can stimulate the hydrolysis of potentially toxic xenobiotics in vivo by specific catalytic antibodies, said compound being characterized in that it is non immunogenic, it comprises a recalcitrant and potentially toxic xenobiotic or a fragment thereof and in that it has a specific affinity for the catalytic site of said antibody.

It also pertains to the use of a non immunogenic recalcitrant xenobiotic or a fragment thereof with a specific affinity for the catalytic site of an antibody, to stimulate hydrolysis of said xenobiotic by said catalytic antibodies.

In accordance with a further implementation of the invention, a compound of the invention is an allergen analogue.

The term "allergen" means any product that can trigger an allergic reaction. An allergen analogue is a molecule the structure of which mimics the allergen but which is non immunogenic. Such allergens in accordance with the invention, by increasing the catalytic activity of antibodies capable of degrading allergens, in particular by hydrolysis, and by indirectly stimulating the production of seric and secretory antibodies, are then susceptible of partially or completely desensitizing an allergic subject.

Consequently, the invention also pertains to a compound that can prevent or diminish an allergic reaction linked to an allergen, characterized in that it comprises a non immunogenic analogue of said allergen and in that it has a specific affinity for the catalytic site of said antibody.

It also pertains to the use of a non immunogenic analogue of an allergen having a specific affinity for the catalytic site of an antibody to prevent or diminish an allergic reaction linked to said allergen.

Any pharmaceutical composition comprising, as the active principle, any compound as described above also falls within the scope of the invention. The term "pharmaceutical composition" means any composition that can be administered to man or to animal. The active principle may if appropriate be associated with another active molecule the function of which is to modulate or stimulate the biological activity of the compound of the invention, or to diminish any secondary effects.

The composition also comprises a pharmaceutically acceptable vehicle.

Vehicles used in preparing pharmaceutical compositions are preferably selected from those generally used in vaccine preparations. Clearly, they are selected as a function of the mode of administration of the composition and its use.

The invention also pertains to the use of a compound in accordance with the invention in preparing a pharmaceutical composition for the treatment or prevention of a disease linked to an enzymatic deficiency.

It also pertains to the use of a compound in accordance with the invention in preparing a composition for stimulating the hydrolysis of xenobiotics, drugs, medication or any other molecule that is potentially toxic to the organism.

It further pertains to the use of a compound of the invention in preparing a composition for the prevention of or for desensitization to allergic reactions.

In addition to their catalytic properties, the Fc region of catalytic antibodies recognize cell receptors, in particular receptors present in cells presenting antigens, cytotoxic cells and macrophages, and more generally the different cells of the immune system. Thus, it is important to emphasize that by stimulating the production of catalytic antibodies by the compounds of the invention, it is possible to target a given catalytic activity on the level of a cell recognizing the catalytic antibody.

When recognition is non specific in type, for example by the Fc regions of antibodies, the catalytic activity can be targeted to cells of the cellular type immune system, this then adding to the action of the humoral system (synthesis of the desired antibodies by the B lymphocytes).

When recognition is specific to a given epitope, i.e., by the Fab'$_2$ paratopic regions, one of the recognized epitopes not being the enzymatic substrate for the catalytic antibody, the compounds of the invention can then target the catalytic activity to a selected target, said target comprising said epitope. In this case, the antibody presents a double specificity, both for a specific epitope and for the enzymatic substrate. The compounds of the invention can thus target a catalytic activity to the effectors of the immune and/or inflammatory system.

Finally, the invention pertains to a method for selecting a compound in accordance with the invention, comprising selecting and isolating a natural catalytic antibody or a catalytic antibody induced by repeated injection of an immunogenic molecule, characterized in that it further comprises the following steps:

a) synthesizing and/or extracting compounds derived from an immunogenic molecule recognized by the isolated catalytic antibody;

b) if appropriate, carrying out a first screening using a biological and/or biochemical test for compounds interacting with the catalytic site of said catalytic antibody;

c) selecting non immunogenic compounds with a specific affinity for the catalytic site of the antibody from compounds synthesized or extracted in step a) or selected in step b), using a test that can measure said affinity.

A number of methods for selecting and isolating a natural catalytic antibody or a catalytic antibody induced by repeated injection of an immunogenic molecule have been described in the prior art and can be used. In particular, the skilled person could refer to scientific publications describing the isolation of natural or induced catalytic antibodies, especially: Blackburn G M and Garcon A (2000), "Biotechnology", Vol 8b, 2$^{nd}$ Edition, Wiley VCH, pp 404–490, and to techniques for isolating monoclonal antibodies that are known to the skilled person, and in particular the hybridoma culture technique developed by Kohler and Milstein (1975).

In step a) of the method of the invention, compounds derived from an immunogenic molecule recognized by the selected catalytic antibody and already isolated are obtained. The compounds can be synthesized in particular by combinatorial chemistry, by biosynthesis or by bioconversion. The chemical structure of the compounds synthesized at a) can also be predicted using bio-informatics methods for predicting chemical structures.

In a particular implementation, the compounds are derived from an immunogenic peptide and are synthesized by mutagenesis of a DNA coding said immunogenic peptide and by expression of the mutated DNA in a host cell using molecular biological methods that are known to the skilled person, such as those described by Sambrook et al (Molecular Cloning: A Laboratory Manual, 3$^{rd}$ edition, Cold Spring Harbor, Laboratory Press, New York, 2001).

If appropriate, in particular when the compounds that are susceptible of interacting with the catalytic site are unknown, the method may comprise a first screening step (step b) of the method) using a biological and/or biochemical test for compounds interacting with the catalytic site of said antibody. That step consists, after generating a large number of compounds derived from the immunogenic compound, in first selecting compounds that have retained the property of binding to the catalytic antibody to reduce the number of compounds to be screened in step c). Any test that can identify compound(s) that specifically interact with a given catalytic antibody from an ensemble of compounds can be used in the method of the invention.

In a particular implementation of the method, the compounds synthesized or extracted in step b) are peptides and are selected using a catELISA type biochemical screening test (Tawfik et al, 1993, supra), screening on a protein array or screening by measuring the surface plasmonic resonance.

A protein array is constituted by a support onto which the different peptides to be screened are bound at set positions. Labeling the catalytic antibody and bringing it into contact with the protein array under conditions that allow protein-protein interactions allow peptides specifically interacting with the catalytic antibody to be selected.

Techniques for measuring the surface plasmonic resonance are known to the skilled person and allow the affinity constants between two molecules to be deduced. Such techniques are easy to carry out, in particular using a BIAcore device (Silin V and Plant A (1997), Trends Biotechnol 15: 353–359).

In general, any biochemical method that allows the interaction of a peptide with an antibody to be tested, and in particular methods derived from Western Blot, can be used in the method of the invention to carry out biochemical screening of compounds interacting with the antibody.

Preferably, methods are selected that can be used routinely and which allow screening of the molecules at a high throughput.

It is also possible to use different biological tests developed to detect molecular interactions to be used, in particular interactions between two peptides or two polypeptides.

In a preferred implementation of the method of the invention, the peptide compounds are selected using a phage display or double-hybrid technique. Those methods are well known to the skilled person and have been described by Sambrook et al (2001, supra).

Of the set of compounds synthesized and possibly selected by the first screening, the compounds of the invention are then selected in step c) of the method, using a test that can measure the affinity for the catalytic site of the antibody.

As an example, a compound of the invention can be selected by measuring the rate of the reaction catalyzed by the catalytic antibody in the presence either of the compound to be tested, or of the immunogenic reference compound. When the rate of the reaction catalyzed by the antibody, measured in the presence of the test compound, is significantly higher than that measured in the presence of the reference immunogenic compound, the test compound is selected.

Consequently, any type of test that can measure the affinity constant of compound-antibody complexed can be used to select the non immunogenic compounds of the invention.

In a further aspect, the invention concerns novel methods for therapeutic treatment.

In particular, the invention pertains to a method:
for the therapeutic treatment or prevention of a disease connected with an enzymatic deficiency;
for stimulating the hydrolysis of xenobiotics, drugs, medication or any other molecule that is potentially toxic to the organism; or
for preventing or desensitizing against allergic reactions.

In all cases, the methods comprise administered to an organism a pharmaceutical composition comprising a compound of the invention as the active principle, alone or in association with a further pharmaceutically active substrate capable of increasing, in vivo, the activity of a catalytic antibody, in combination with a pharmaceutically acceptable vehicle.

The modes of administration, the composition of the vehicle and the dosage of the administered compounds for the treatment will be selected as a function of the desired therapeutic or preventative effect. Depending on the case, the forms of administration can be local or systemic, in particular oral, sublingual, intravenous, nasal, aerosol, intramuscular, subcutaneous or alimentary.

It should be noted that since the treatment methods of the invention are generally vaccination methods, the skilled person will in particular use vehicles that are conventionally used in that field.

The following examples illustrate certain modes of implementation of the invention without being limiting in nature.

KEY TO FIGURES

FIG. 1: FIG. 1 illustrates the induced fit mechanism allowing a non immunogenic compound to displace the equilibrium of conformational states of a catalytic antibody from less active or inactive catalytic forms towards active isomeric forms. In vivo, displacement of the equilibrium results in an increase in the catalytic activity of the catalytic antibody and indirectly in stimulation of production.

EXAMPLES

Example 1

Compound Capable of Increasing the Catalytic Activity of Secreted IgA Directed Against Epitopes of the Herpes Virus to Combat Herpes Virus Infections Secreted IgAs are the principal effectors of the mucosal immune system. They are involved in recognizing bacterial, viral or protozoic antigens. It has in particular been shown that IgA extracted from healthy mother's milk may have catalytic protein kinase, DNase or RNase type activities (Buneva V N et al, (1998), Appl Biochem Biotechnol 75: 63–76, Nevinsky G A et al (1998) Appl Biochem Biotechnol 75: 77–91).

Included in secreted IgA, the production of a catalytic antibody directed against the epitopes of the Herpes simplex type 1 virus could be stimulated by cutaneous application of non immunogenic peptides in the form of patches. The selected non immunogenic peptides represent specific sequences of known HSV1 epitopes.

A similar approach can be applied to stimulate the production of catalytic antibodies hydrolyzing HSV2 peptides, responsible for genital herpes or Zoster herpes, responsible for shingles.

Example 2

Compound Capable of Increasing the Catalytic Activity of an Antibody Hydrolyzing Certain Peptide Sequences of TNFα in the Treatment of Rheumatoid Arthritis TNFα (tumour necrosis factor) is a cytokine which plays a central role in inflammatory conditions encountered in autoimmune diseases such as rheumatoid arthritis or autoimmune myocardia. It also acts as a regulator for other pro-inflammatory cytokines. The inflammatory action of TNFα is linked to its binding to two cell receptors, p55 and p75. This binding employs loops of TNFα formed by residues 29–34, 84–91 and 143–148.

Non immunogenic peptides having a specific affinity with a catalytic antibody capable of hydrolyzing TNFα were selected from peptides containing the sequences LNRRA (29–33), IASVY (83–87) and LFA (143–145). Repeated injection of these peptides to a patient suffering from rheumatoid arthritis should stimulate in vivo the production of catalytic antibodies hydrolyzing TNFα in sequences recognizing cell receptors, thus reducing inflammatory mechanisms linked to rheumatoid arthritis.

Example 3

Compound Capable of Increasing the Catalytic Activity of an Antibody Hydrolyzing Cocaine to Treat Drug Tolerance Phenomena The consumption of drugs by a subject provokes a tolerance phenomenon. The quantity of a drug circulating in the blood after administration is directly linked to the narcotic effect and to the tolerance that follows. Immunizing a subject using immunogenic peptides directly stimulating the production of catalytic antibodies hydrolyzing cocaine can diminish or eliminate the quantity of circulating cocaine. In order to increase the catalytic activity of these antibodies and to indirectly stimulate their production, small concentrations of codeine, a non immunogenic compound close to cocaine, could be repeatedly injected intravenously.

Example 4

Compound Capable of Increasing the Catalytic Activity of an Antibody With β-Lactamase Activity The development of catalytic antibodies from enzymatic active sites using an idiotypic network has been demonstrated (Avalle B et al, Faseb J (1998) 12: 1055–1060). In particular, starting from the active site for β-lactamase, a specific antibody (Ab1) was obtained which inhibited β-lactamase activity (Kosnikov et al, PNAS (2000) 97: 13526–13531). This antibody allowed the production of a second generation of Ab2 antibodies, which were anti-idiotypic, and had an activity close to that of β-lactamase.

Thus, the lethality linked to repeated injection of penicillin should be reduced by stimulating the production of anti-idiotypic antibodies with a β-lactamase activity by administering non immunogenic peptides mimicking the paratope of the antibody induced in the presence of the active site for β-lactamase.

Example 5

Compound Capable of Increasing the Catalytic Activity of an Antibody Hydrolyzing an Allergen to Diminish or Prevent an Allergic Reaction.

Specific desensitization induces both an increase in seric and secretory blocking antibodies, a reduction in the production of specific IgE and a modification in the mastocyte and basophile response as well as that of lymphocytes.

Administering a non immunogenic molecule derived from the allergen to a subject sensitive to an allergen should modify the immunological response and increase the production of catalytic antibodies directed against said allergen, an indirect increase in the production of seric and secretory blocking antibodies and a reduction in the production of specific IgEs, because of hydrolysis of the allergen. This set of responses can diminish or prevent the allergic reaction.

The three examples below illustrate this application:

A. Non Immunogenic Peptides for Preventing or Diminishing Allergies to Anti-Infectious Medication.

Antibiotics are molecules that are most often incriminated in allergic reactions to anti-infectious medication (50% of cases). It is known that allergenicity is primarily carried by the β-lactame cycle. By being cleaved during metabolism, the β-lactame cycle produces the penicilloyl hapten which is capable of inducing the production of IgE.

It would thus be possible, using orally injected non immunogenic peptides that inhibit β-lactamase, to induce the production of non IgE antibodies capable of hydrolyzing antibiotics with a β-lactame ring, thus preventing the production of IgE antibodies.

B. Non Immunogenic Peptides Stimulating the Production of Catalytic Antibodies Hydrolyzing Serotonin to Prevent or Diminish Food Allergies.

For a number of years, we have observed an alarming increase in food allergies. That phenomenon has appeared concomitantly with a modification in our eating habits: we are observing a large increase in the quantity of certain histamino-liberating mediators in our fresh food: histamine, serotonin, tyramine, etc. Those products can circulate in the blood, even more so when the intestinal wall is immature (a young child), and can induce allergic phenomena by cell mediation. Serotonin (5-hydroxytryptamine), for example, is derived from tryptophan and degraded into 5-hydroxyindole acetate.

It would thus be possible to select non immunogenic peptides derived from serotonin and having a specific activity for a catalytic antibody hydrolyzing serotonin. Oral injection of such peptides stimulating the production of catalytic antibody degrading excess serotonin should reduce allergic phenomena linked to food.

C. Non Immunogenic Peptides Stimulating the Production of Catalytic Antibodies Hydrolyzing Peanut Proteins Peanut allergies affect an increasing number of individuals. The seriousness of the shocks they cause and their frequency are increasing. Of the many allergens detected but not characterized, one 17 kD protein, Ara h II, has been identified as the major allergen, and has been characterized. Comparisons of the sequences have allowed sequence homologies to be identified with proteins of different foods of the legume family which could cause cross sensitivities.

Oral absorption of such non immunogenic peptides stimulating the production of catalytic antibodies degrading proteins of legumes responsible for said allergies should reduce such allergic phenomena.

The invention claimed is:

1. A compound that modulates the activity of a catalytic antibody, wherein said compound has a specific affinity for a catalytic site of said antibody, is non immunogenic, and is a ligand that binds to a receptor, said compound being a peptide consisting of amino acid sequence LNRRA (SEQ ID NO:1).

2. The compound according to claim 1, wherein said peptide is derived from the cytokine TNF-α.

3. A pharmaceutical composition comprising, as the active principle, the compound according to claim 1 in combination with a pharmaceutically acceptable vehicle.

4. The pharmaceutical composition according to claim 3, wherein said composition comprises a further active molecule that modifies or stimulates the biological activity of said compound or diminishes any secondary effects of said compound.

5. The compound of claim 1, wherein said ligand is a hormone, a drug, or a medication.

* * * * *

SEQUENCE LISTING

<160> NUMBER OF SEQ ID NOS: 2

<210> SEQ ID NO 1
<211> LENGTH: 5
<212> TYPE: PRT
<213> ORGANISM: Homo sapiens

<400> SEQUENCE: 1

Leu Asn Arg Arg Ala
 1               5

<210> SEQ ID NO 2

```
-continued

<211> LENGTH: 5
<212> TYPE: PRT
<213> ORGANISM: Homo sapiens

<400> SEQUENCE: 2

Ile Ala Ser Val Tyr
1               5
```